(12) United States Patent
Burnham et al.

(10) Patent No.: US 10,086,160 B2
(45) Date of Patent: Oct. 2, 2018

(54) MASK VENT

(75) Inventors: Robert Thomas Burnham, Fairlight (AU); Nicolas Lo Grandjean-Thomsen, Enfield South (AU); Martin Kang, Strathfield (AU)

(73) Assignee: ResMed Limited, Bella Vista (AU)

( * ) Notice: Subject to any disclaimer, the term of this patent is extended or adjusted under 35 U.S.C. 154(b) by 656 days.

(21) Appl. No.: 13/985,737

(22) PCT Filed: Feb. 15, 2012

(86) PCT No.: PCT/AU2012/000143
§ 371 (c)(1),
(2), (4) Date: Aug. 15, 2013

(87) PCT Pub. No.: WO2012/109704
PCT Pub. Date: Aug. 23, 2012

(65) Prior Publication Data
US 2013/0327336 A1   Dec. 12, 2013

Related U.S. Application Data

(60) Provisional application No. 61/443,422, filed on Feb. 16, 2011, provisional application No. 61/628,300, filed on Oct. 28, 2011.

(51) Int. Cl.
| | |
|---|---|
| A61M 16/06 | (2006.01) |
| A61M 16/08 | (2006.01) |
| A61M 16/20 | (2006.01) |

(52) U.S. Cl.
CPC ........ *A61M 16/06* (2013.01); *A61M 16/0816* (2013.01); *A61M 16/0866* (2014.02); *A61M 16/20* (2013.01); *A61M 2205/42* (2013.01)

(58) Field of Classification Search
CPC .............. A61M 16/06; A61M 16/0866; A61M 16/0816; A61M 2205/42; A61M 16/20;
(Continued)

(56) References Cited

U.S. PATENT DOCUMENTS

| | | | |
|---|---|---|---|
| 2006/0266365 A1 | 11/2006 | Stallard | |
| 2007/0095350 A1 | 5/2007 | Darkin et al. | |

(Continued)

FOREIGN PATENT DOCUMENTS

| | | |
|---|---|---|
| CN | 1623609 | 6/2005 |
| CN | 1901962 | 1/2007 |

(Continued)

OTHER PUBLICATIONS

Third Office Action issued in corresponding Chinese Patent Application No. 201280018599.0 dated Mar. 7, 2016, with English translation therefore.

(Continued)

*Primary Examiner* — Annette Dixon
(74) *Attorney, Agent, or Firm* — Nixon & Vanderhye P.C.

(57) ABSTRACT

A vent arrangement is provided to a mask to discharge exhaled gas from the mask to atmosphere. The vent arrangement is structured to diffuse the exhaust vent flow to produce less air jetting, thereby increasing the comfort of the patient and their bed partner. The vent may include a first wall, a second wall defining an outer perimeter, and a plurality of gas washout vent holes positioned between the first wall and the second wall, the vent holes having an inner edge positioned within the outer perimeter of the second wall.

52 Claims, 17 Drawing Sheets

(58) Field of Classification Search
CPC .............. A61M 16/00; A61M 16/0051; A61M 16/0057; A61M 16/0066; A61M 16/009; A61M 16/0463; A61M 16/0616; A61M 16/0622; A61M 16/0633; A61M 16/0638; A61M 16/065; A61M 16/0666; A61M 16/0683; A61M 16/08; A61M 16/0825; A61M 16/0858; A61M 16/0875; A61M 16/1055; A61M 16/1065; A61M 16/16; A61M 16/208; A61M 2202/0085; A61M 2202/0225; A61M 2205/0205; A61M 2205/0238; A61M 2205/3331; A61M 2205/43; A61M 2205/44; A61M 2205/581; A61M 2205/582; A61M 2205/583; A62B 9/04
USPC ............ 128/206.21, 200.24, 202.27, 204.18, 128/205.11, 205.12, 205.19, 205.24, 128/205.25, 206.24, 206.28, 207.11, 128/207.13, 912
See application file for complete search history.

(56) References Cited

U.S. PATENT DOCUMENTS

2007/0267023 A1* 11/2007 Ging ..................... A61M 16/06
128/206.21
2009/0050156 A1* 2/2009 Ng ........................ A61M 16/06
128/205.24

FOREIGN PATENT DOCUMENTS

| CN | 101380497 | 3/2009 |
|---|---|---|
| JP | 2009-50707 A | 3/2009 |
| WO | WO 2007/053878 | 5/2007 |
| WO | WO 2010/067237 | 6/2010 |
| WO | WO 2010/135785 | 12/2010 |
| WO | WO 2011/022751 | 3/2011 |
| WO | WO 2012/109704 | 8/2012 |

OTHER PUBLICATIONS

First Office Action issued in corresponding Chinese Appln. No. 201280018599.0 dated Mar. 26, 2015, with English translation thereof.
First Examination Report issued in corresponding New Zealand Application No. 614200 dated Mar. 14, 2014.
Notice of Acceptance issued in corresponding Australian Application No. 2012219019 dated Jun. 22, 2015.
Extended European Search Report issued in corresponding European Appln. No. 12 74 7629.9 dated Jun. 30, 2015.
Further Examination Report issued in corresponding New Zealand Application No. 614200 dated Jun. 30, 2015.
First Examination Report issued in corresponding New Zealand Application No. 708938 dated Jun. 30, 2015.
International Preliminary Report on Patentability issued in corresponding PCT Application No. PCT/AU2012/000143 dated Aug. 21, 2013.
International Search Report for PCT/AU2012/000143, dated May 2, 2012.
Patent Examination Report No. 1 issued in corresponding Australian Appln. No. 2012219019 dated Aug. 27, 2014.
Second Office Action issued in corresponding Chinese Application No. 201280018599.0 dated Sep. 23, 2015, with English translation thereof.
First Office Action issued in corresponding Japanese Application No. 2013-553743 dated Dec. 21, 2015 with English translation thereof.
International Preliminary Report on Patentability along with a Written Opinion issued in corresponding PCT Application No. PCT/AU2012/000143 dated Aug. 21, 2013.
Decision of Rejection issued in a corresponding Japanese Patent Application No. 2013-553743 dated Aug. 29, 2016, with English language translation thereof.
First Examination Report issued in corresponding New Zealand Application No. 720474 dated Jun. 20, 2016.
Communication dated Mar. 16, 2017 issued in European Application No. 12 747 629.9 (6 pages).
Second Office Action dated Dec. 4, 2017 issued in Japanese Application No. 2013-553743 with English translation (16 pages).
First Examination Report dated Dec. 11, 2017 issued in New Zealand Application No. 737320 (5 pages).

* cited by examiner

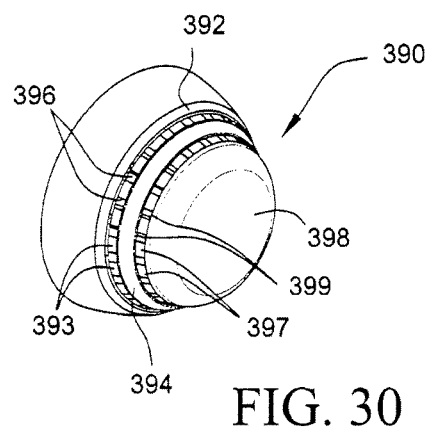
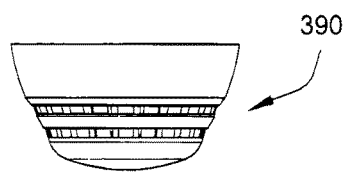
FIG. 31
FIG. 30
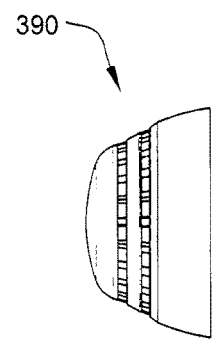
FIG. 32
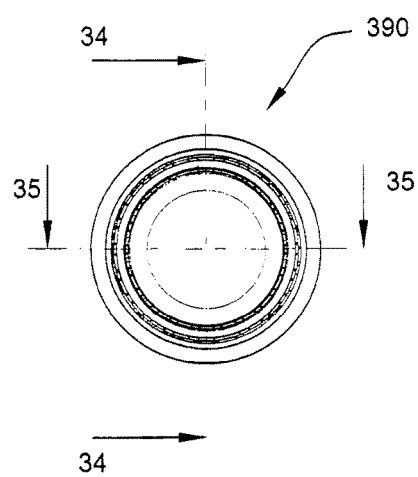
FIG. 33

MASK VENT

CROSS-REFERENCE TO APPLICATION

This application is the U.S. national phase of International Application No. PCT/AU2012/000143, filed Feb. 15, 2012, which designated the U.S. and claims the benefit of U.S. Provisional Nos. 61/443,422, filed Feb. 16, 2011, and 61/628,300, filed Oct. 28, 2011, the entire contents of each which are incorporated herein by reference in its entirety.

FIELD OF TECHNOLOGY

The present technology relates to mask vents used for Non-invasive Positive Pressure Ventilation (NIPPV) and for continuous positive airway pressure (CPAP) therapy of sleep disordered breathing (SDB) conditions such as obstructive sleep apnea (OSA).

BACKGROUND OF TECHNOLOGY

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A gas washout vent on the mask or conduit discharges the exhaled gas from the mask to atmosphere.

The washout vent is normally located on the mask, such as on the frame, on an elbow connected to the mask, or near the mask in the gas delivery conduit coupled to the mask. The washout of gas through the vent to the atmosphere removes exhaled gases to prevent carbon dioxide build-up, and hence "rebreathing", which represent a health risk to the mask wearer. Adequate gas washout is achieved by selecting a vent size and configuration that allows a minimum safe washout flow at a low operating CPAP pressure, which typically can be as low as 4 cm $H_2O$ for adults and 2 cm $H_2O$ for children. A typical range is between 2-30 cm $H_2O$, while a typical treatment pressure is about 8-12 cm $H_2O$ for adults.

Noise is a significant issue in CPAP treatment for the patient and/or the patient's bed partner. Excessive noise can lead to patients being non-compliant with the CPAP therapy. One source of noise is the exhaust through the vent in the mask or conduit. The flow of gas through the vent creates noise as it exits to and interacts with the atmosphere. Noise can adversely affect patient and bed-partner comfort, depending on both the magnitude and character of the noise. Further, bi-level gas delivery therapies tend to generate more noise than do constant level gas delivery regimes. This is thought to be due to the extra turbulence created by the gas accelerating and decelerating as it cycles between relatively low and relatively high pressures in the bi-level gas delivery systems.

"Air Jetting" out of the vents is also a significant issue. Air jetting, or lack of diffusion in the vent, involves a high-velocity jet stream of exhaust gases blowing onto obstacles (such as bedding, bed partner, or even onto the mask wearer themselves). This not only causes a significant increase in noise due to a sudden change in velocity of the exhausted air, but the high-velocity jet stream also creates great discomfort for the bed partner or mask wearer as a result of "wind chill". Accordingly, a plurality of diffuse vent holes may be used.

For example, FIG. 19 illustrates a prior art elbow 260 having a gas washout vent 262, which includes a plurality of diffuse vent holes 266. This gas washout vent 262 is further described in U.S. patent publication 2009/0050156, published Feb. 26, 2009, which is incorporated herein by reference in its entirety. FIGS. 20 and 21 illustrate a perspective view and a cross-sectional view, respectively, of the gas washout vent 262.

The gas washout vent 262 includes a first or bottom wall 264, a second or top wall 268, a plurality of supports 270 extending between the first wall 264 and the second wall 268, and a plurality of vent holes 266 formed between the supports 270. The supports 270 are disposed on an outer edge of the second wall 268 extending outward from the second wall 268, and are disposed on an upper surface of the first wall 264. The vent holes 266 form passageways allowing escape of the washout gas.

While the vent arrangement of FIGS. 19-21 works in a satisfactory manner for its intended purpose, a need has developed to even better vent to deal with the possibility of moisture in the exhausted air. The moisture may tend to bead around the vent holes, in particular on the surfaces immediately outside of the vent holes. The beads of water may vibrate as the exhaust gases rush through the vent holes and past the beads of water, causing a whistling noise. Additionally, the water beads may cause a partial obstruction of the vent holes further contributing to vent noise.

SUMMARY OF TECHNOLOGY

One aspect of the present technology relates to a vent for a mask providing diffuse venting of gas.

Another aspect of the present technology relates to a vent for a mask that produces low noise levels under humidification.

Another aspect of the present technology relates to a vent for a mask that substantially prevents moisture accumulating around a vent hole.

Another aspect of the present technology relates to a vent insert for a mask that is insertable on the mask in more than one location. For example, the vent insert may be inserted on a frame or an elbow of the mask.

Another aspect of the present technology relates to a vent for a mask. The vent includes a first wall, a second wall defining an outer perimeter, and one or more gas washout vent openings positioned between the first wall and the second wall, the vent openings having an inner edge positioned inside or within the outer perimeter of the second wall.

The first wall may be formed as part of, e.g., in one piece, with the frame, elbow or other portion to which it is attached. Also, the vent may take the form of a vent that can be removed from the frame, elbow or other attachment point on the mask.

Another aspect of the present technology relates a vent for a mask. The vent includes a first wall having an inner side surface and a top surface, a second wall having a top surface and a bottom surface, one or more spaced supports disposed between the first wall and the second wall, each support having an upper face disposed adjacent to the bottom surface of the second wall, and a side face disposed adjacent to the inner side surface of the first wall, and one or more vent holes disposed between each of the supports.

Another aspect of the present technology relates to a vent for a mask, the vent including a first wall, a dome shaped portion, a first row of vent holes provided to the dome portion, and a second row of vent holes provided to the dome portion, the first row of vent holes being displaced from the second row of vent holes.

Another aspect of the present technology relates to a vent arrangement for a mask, the vent arrangement including a vent cap, the vent cap including a first wall and a dome portion extending upwardly from the first wall, the dome portion including a second wall and a plurality of spaced supports extending between the first wall and the second wall, and a one or more vent holes, at least one of the vent holes provided between each of the supports, wherein the supports gradually decrease in width moving away from a central axis of the vent cap.

Another aspect of the present technology relates to a vent for a mask, the vent including a first wall having a side surface, a second wall having a concave upper surface and a lower surface forming a baffle, a plurality of spaced supports disposed between the second wall and the first wall, and a plurality of vent holes, at least one of the vent holes disposed between each of the supports, wherein an air flow chamber formed between the side surface of the lower wall and the baffle gradually decreases in width as air flows towards the vent holes.

Another aspect of the present technology relates to a vent for a mask, the vent including a side wall, a baffle provided inside the side wall, the baffle having a concave second surface, and a plurality of inwardly facing vent holes provided between the side wall and the baffle.

Another aspect of the present technology relates to a vent for a mask, the vent including a first wall, a second wall, a plurality of supports disposed between the first wall and the second wall, and at least one gas washout vent hole positioned between the supports, the supports and vent hole being positioned relative to the first wall and the second wall to reduce noise and to prevent moisture from forming on or adjacent the vent during gas washout.

Another aspect of the present technology relates to a vent for a mask including a first wall, an intermediate wall, a second wall, a first row of supports disposed between the first wall and the intermediate wall, a first row of vent holes with each of the vent holes disposed between adjacent first supports, a second row of supports disposed between the intermediate wall and the second wall, and a second row of vent holes with each of the vent holes disposed between adjacent second supports.

Another aspect of the present technology relates to a mask, the mask including a frame, an interface provided to the frame and one or more of the vents described above.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 2b is a cross-sectional view of the gas washout vent of FIG. 2a;

FIG. 30 is a perspective view of a gas washout vent according to an example of the present technology;

FIG. 31 is a top view of the elbow of FIG. 30;

FIG. 32 is a side view of the elbow of FIG. 30;

FIG. 33 is a front view of the elbow of FIG. 30;

DETAILED DESCRIPTION OF ILLUSTRATED EXAMPLES

The following description is provided in relation to several examples (some of which are illustrated, some of which may not) which may share common characteristics and features. It is to be understood that one or more features of any one example may be combinable with one or more features of the other examples. In addition, any single feature or combination of features in any of the example or examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices or blowers described herein may be designed to pump fluids other than air.

1. Mask Examples

A range of masks (also referred to as patient interfaces or mask systems) are known including nasal-masks, nose & mouth masks, full-face masks and nasal prongs, pillows, nozzles & cannulae.

Masks typically include a rigid or semi-rigid portion (often referred to as a shell or frame) and a soft, patient contacting portion adapted to form a seal with the patient's nose and/or mouth (often referred to as a cushion or nasal prong arrangement). An elbow may be provided to the mask or frame and be adapted to connect to an air delivery tube that delivers breathable gas to the patient. However, it should be appreciated that other mask arrangements are possible, e.g., not rigid (e.g., constructed of cloth).

One or more gas washout vents are provided to the mask, elbow or associated conduit to discharge gas exhaled by the patient from the mask to the atmosphere. In examples, the one or more vents may be provided to the frame and/or to the elbow of the mask. One or more vents in the associated conduit are also possible.

Figure 1A:
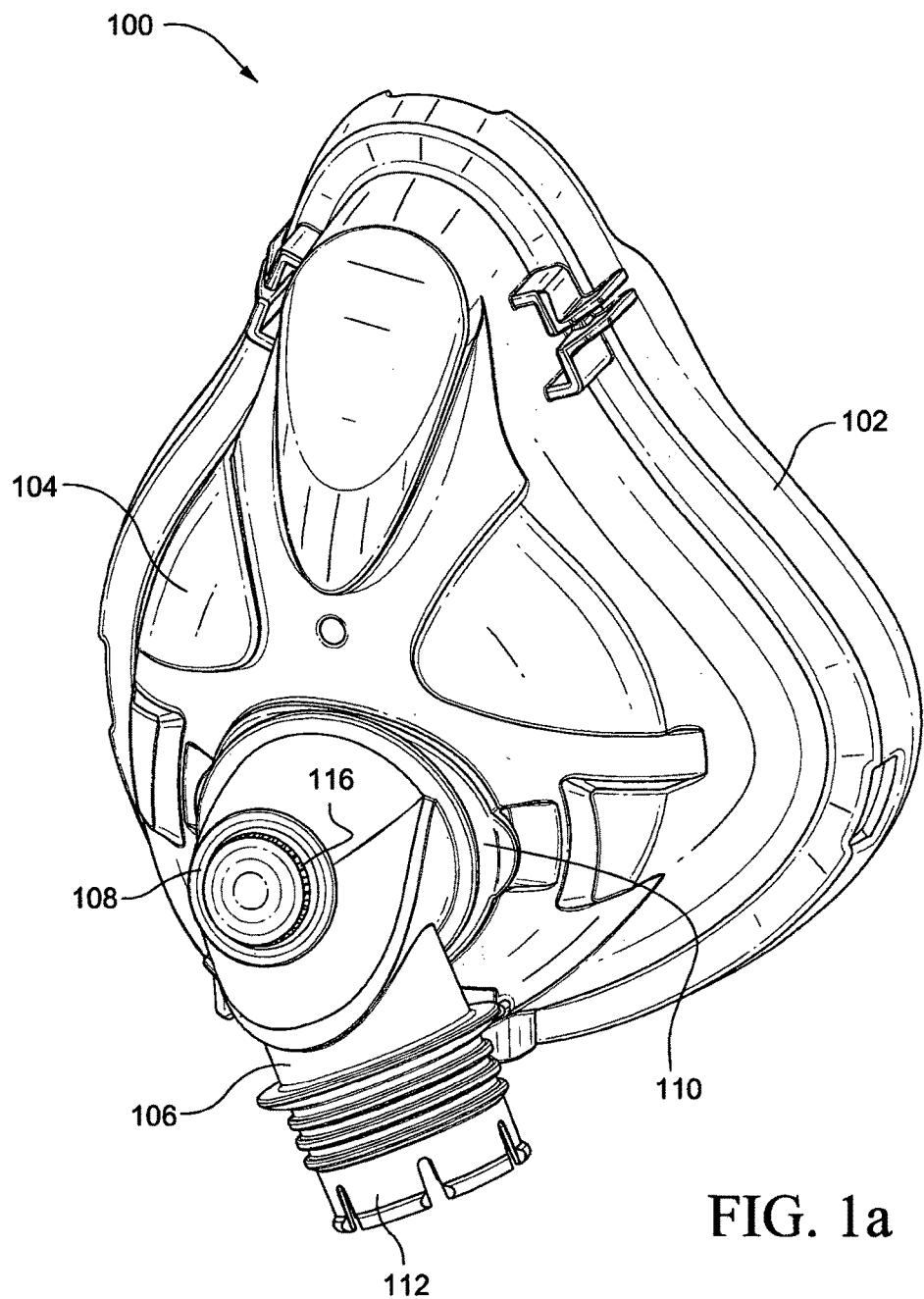
FIG. 1a is a perspective view illustrating a mask with a gas washout vent according to an example of the present technology.
Figure 1B:
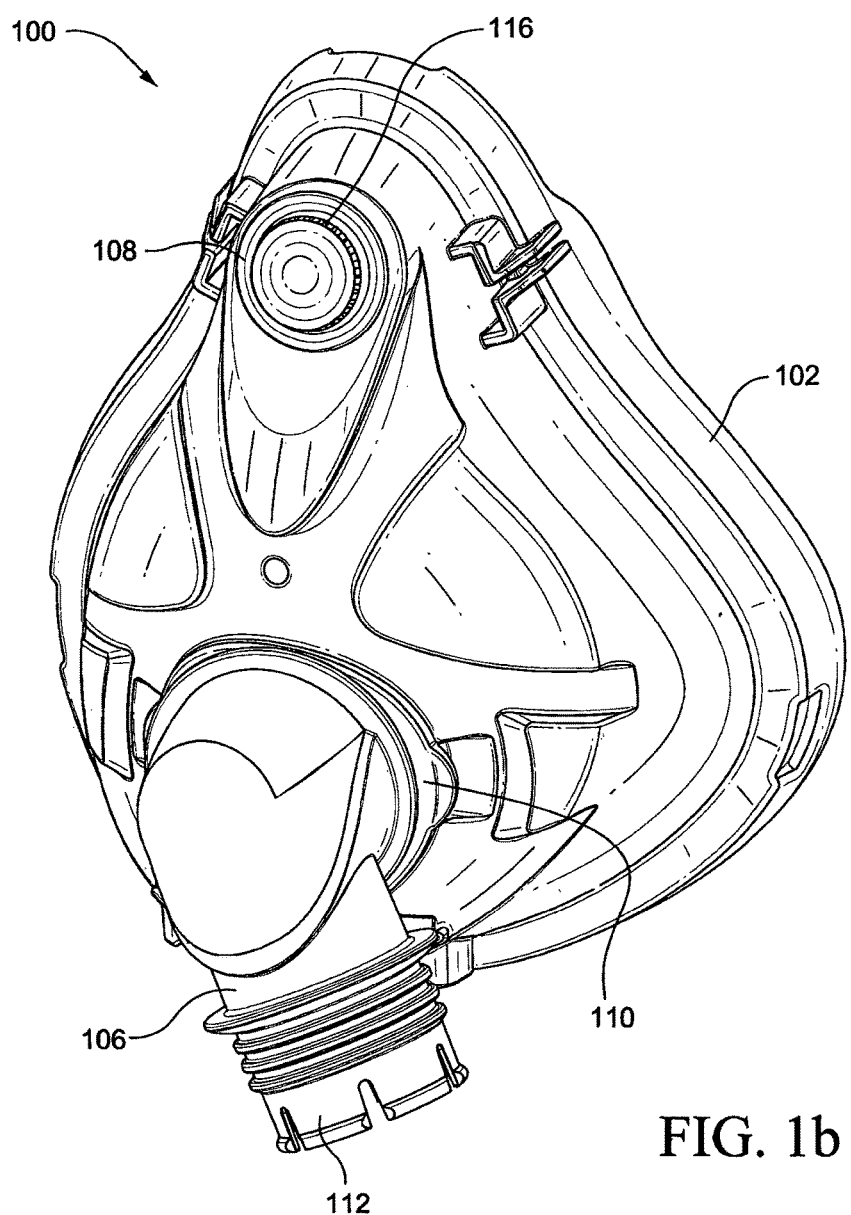
FIG. 1b is a perspective view illustrating a mask with a gas washout vent according to an example of the present technology.

FIGS. 1a and 1b illustrate a mask 100 that may be used with examples of the present technology. The mask 100 is a full-face CPAP mask, although, as noted above, other types of masks may be used, including nasal masks, nose & mouth masks, nasal prongs, pillows, nozzles & cannulae. The mask 100 includes a cushion 102 adapted to form a seal with the patient's face, and a frame 104. The mask 100 may include headgear connectors (not shown) adapted to connect to headgear to secure the mask 100 to the patient's head.

An elbow 106 includes a first end 110 adapted to connect to an opening in the frame 104 and a second end 112 adapted to connect to an air delivery tube (not shown), the air delivery tube adapted to deliver breathable gas through the elbow 106 to an interior of the mask 100. The elbow 106 may be a rotatable elbow, and may be removable from the mask 100.

The mask 100 may include one or more gas washout vents, which may be in the form of a vent, vent insert, or vent cap 108. The vent cap 108 includes a plurality of vent holes 116 adapted to discharge gas exhaled by the patient from the mask 100 to the atmosphere. The vent cap 108 is positioned on the elbow 106 in the example of FIG. 1a, and is positioned on the frame 104 in the example of FIG. 1b. In either instance, the vent cap 108 may be removable from the mask 100, or may be permanently attached to or otherwise formed in one piece with the mask 100.

2. Vent Cap

The following describes alternative examples of vent arrangements for gas washout from a mask. It should be appreciated that each vent cap may be adapted for use with any suitable interface type, e.g., nasal masks, nose & mouth masks, full-face masks, nasal prongs, nozzles, etc. In addition, each vent cap may be adapted for use in any suitable portion of the mask, e.g., frame, elbow, conduit, etc.

In an example, the vent arrangement may be a common component structured for use in multiple interface types. For example, the vent arrangement may be adapted for use in a mask elbow, a mask frame for a full-face mask, and/or a frame for a nasal mask or prong/nozzle arrangement. The vent below may be structured to diffuse the exhaust vent flow. Increased diffusion of the exhaust vent flow may cause less air jetting onto bed clothes and bed partners, and may also produce less noise.

In the illustrated examples, the vent or vent cap is generally circular. However, the vent caps may have any suitable shape, e.g., elliptical. Also, the vent caps may not form a completely closed shape, e.g., the vent caps may be hemispherical or semi-circular. This arrangement may allow for passage of another apparatus (e.g., anti-asphyxia valve (AAV)) or easier insertion and removal of the vent cap.

In addition, the vent cap may be removably attachable or formed with the portion of the mask on which it resides.

2.1 Supports Inside of Vent Perimeter

Figure 2A:
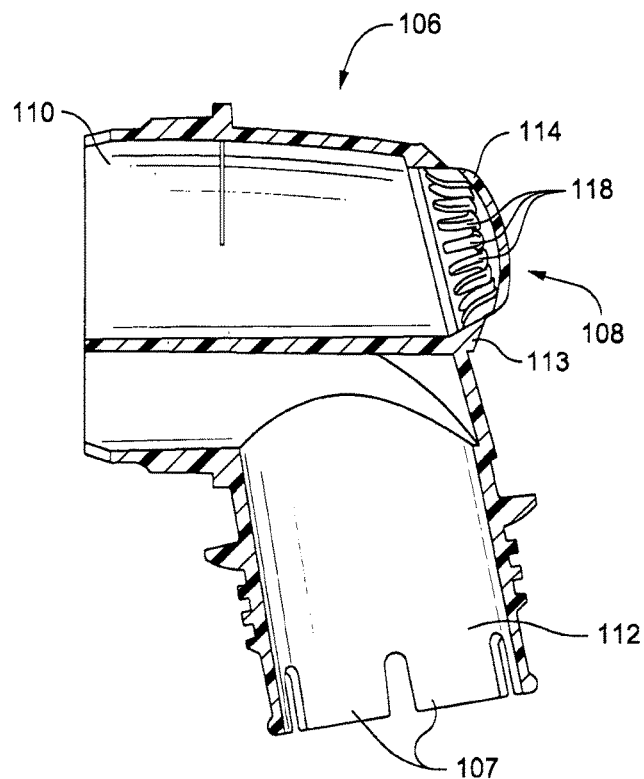
FIG. 2a is a cross-sectional view illustrating an elbow with a gas washout vent according to an example of the present technology.

FIG. 2a illustrates a cross-sectional view of the elbow 106, including the vent cap 108. The elbow 106 includes a first end 110 adapted to connect to an opening in the mask, and a second end 112 adapted to connect an air delivery tube (not shown). The second end may have a one or more resilient flexible arms 107 adapted to engage with the air delivery tube or a swivel connector positioned between the elbow 106 and the air delivery tube.

Figure 2B:
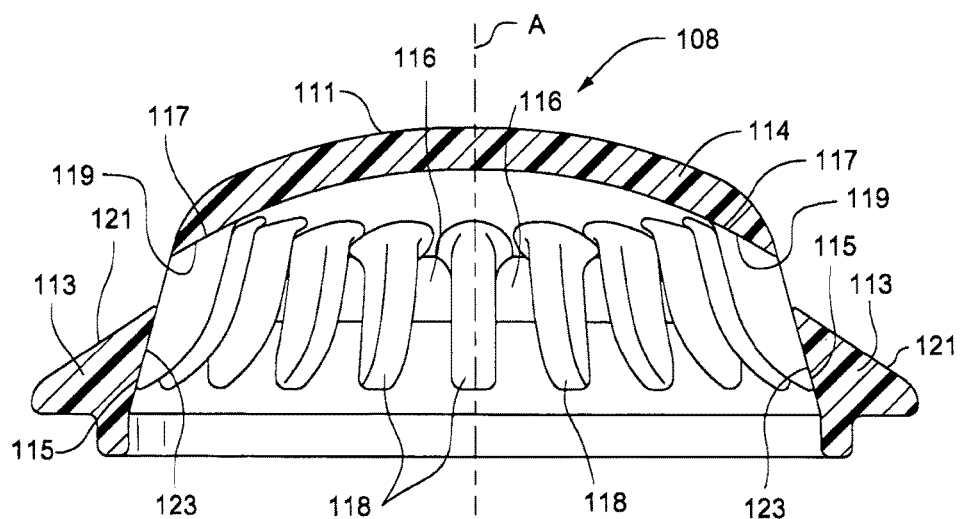

FIG. 2b illustrates an enlarged cross-sectional view of the vent cap 108. The vent cap 108 includes a central axis A, a first wall 113 that may be a lower wall or at the base or first region of the vent cap, a second wall 114 that may be an upper wall, dome, or second region of the vent cap, and a plurality of supports 118 disposed between the first wall 113 and the second wall 114. A plurality of vent holes 116 are formed between the supports 118, each vent hole 116 including a passage or groove between an inner portion and an outer portion of the vent cap 108. The outer edge of the second wall 114 defines an outer perimeter. The vent holes 116 have an inner edge disposed inside the outer perimeter of the second wall 114.

The vent cap 108 has a circular dome shape, although the second wall 114 may be flat instead of domed, and other shapes may be used. Preferably, the second wall may be shaped to aid in moving any accumulated water droplets away from the vent holes, for example a rounded shape may direct the water droplets in a certain direction. In addition, the shape of the second wall may dictate or aid the direction that air exits the vent holes. For example, the dome shape as shown on FIGS. 2a and 2b may encourage the air to exit the vent holes and travel along top face 121, thereby diffusing or fanning the vent flow around the vent cap 108 and in a direction generally towards the patient. This may also assist in preventing the bed partner having air jetting in their direction during therapy. The vent holes 116 may be spaced around the exterior of the vent cap 108 between the first wall 113 and the second wall 114 to diffuse the gas washout exiting from the vent holes 116. The vent holes may be uniformly spaced, and have a uniform size and/or shape. Alternatively, the vent holes may be randomly disposed on vent cap 108.

The first wall 113 has a side face 115 and a top face 121. The side face 115 may be angled inwardly moving from a bottom of the side face to a top of the side face. The top face may be downwardly angled moving away from the side face 115 and away from the central axis A. Top face 121 may be sloped or angled to aid in driving any accumulated water droplets away for the vent holes 116. Side face 115 may be shaped to aid in manufacture of the component (i.e., if it is angled inwardly toward central axis A as shown in FIG. 2b, this may permit a line of draw for a tool).

The second wall 114 has a top surface 111 and a bottom surface 117, both of which may be downwardly angled or curved moving away from the center of the second wall 114. The outer edge of the second wall 114 may be tapered to be thinner at the outer edge than a remainder of the second wall. The outer edge of the second wall 114 defines a perimeter of the vent cap 108.

The support walls 118 have a top face 119, and outer side faces 123. The top face 119 is downwardly angled moving away from a center of the vent cap 108, and the top face 119 is angled to match the downwardly angled bottom surface 117 of the second wall 114. The side faces 123 are inwardly angled moving from a bottom of the side faces 123 to a top of the side faces 123. The vent holes 116 are disposed between the support walls 118. The support walls 118 are disposed beneath the bottom surface 117 of the second wall 114, and the top face 119 of the support walls 118 may be in contact with the bottom surface 117 of the second wall 114, although another layer could be disposed in between the bottom surface 117 and the top face 119.

By placing the support walls 118 beneath the second wall 114 and inside the first wall 113, beads of water cannot collect on the support walls 118, since the air pressure from inside the elbow will force the water beads outward on off the support walls 118. This reduces noise that would be produced from water beads that might otherwise collect on the support walls 118.

Additionally, because the top surface 111 of the second wall 114 is downwardly angled or curved, and the top face 121 of the first wall 113 is downwardly angled, any water beads that may be on these surfaces are more likely to run off as opposed to if these surfaces were flat. The tapering of the edges of the second wall 114 also contributes to the running off of any water beads.

Figure 3:
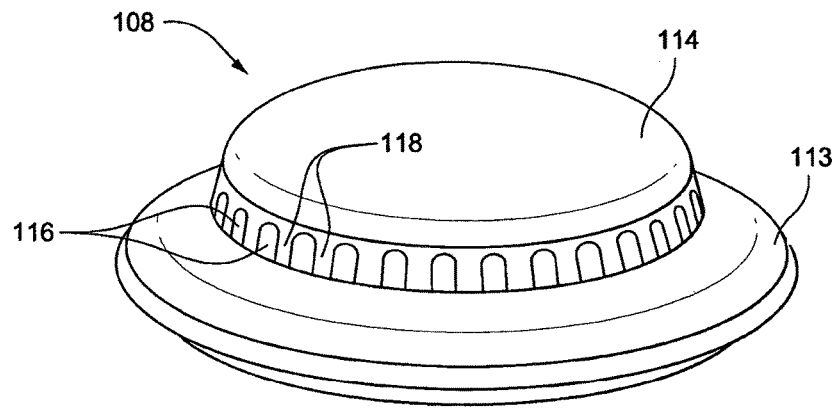
FIG. 3 is a perspective view of a gas washout vent according to another example of the present technology.
Figure 4:
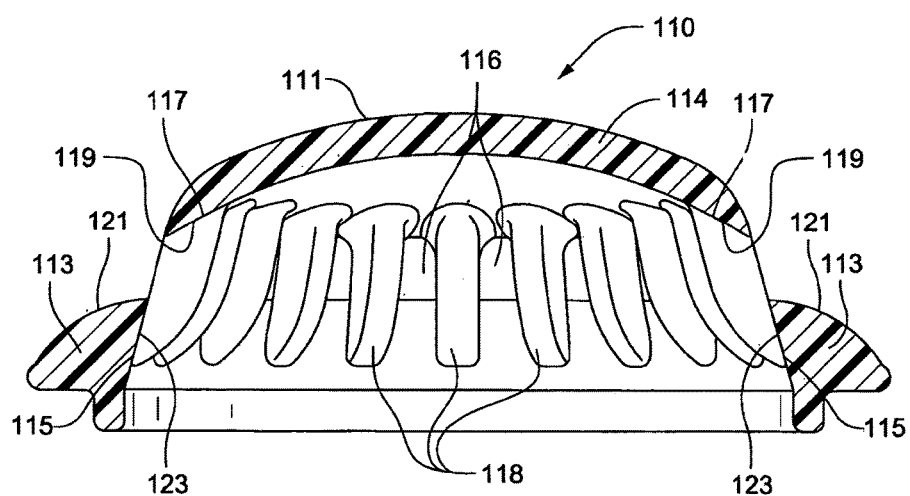
FIG. 4 is a cross-sectional view of a gas washout vent.

FIGS. 3 and 4 illustrate another example in which the top face 121 of the first wall 113 is not only downwardly angled, but the top face 121 is curved. The curved top face 121 may further enhance runoff of any water beads.

2.2 Tapered Supports

Figure 5:
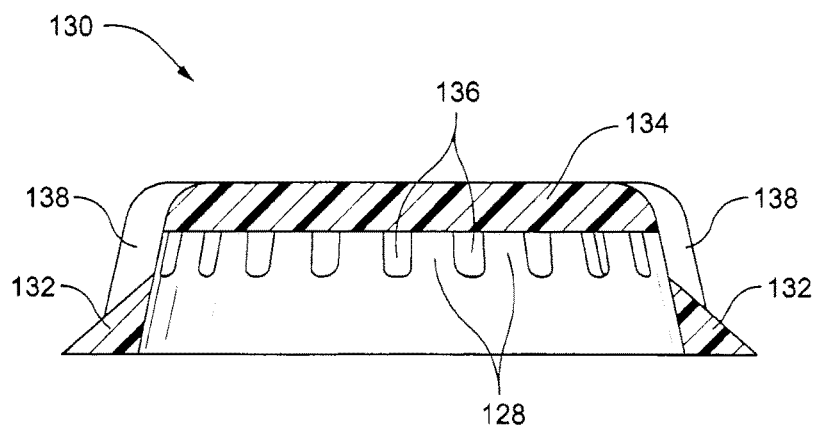
FIG. 5 is a cross-sectional view of a gas washout vent according to another example of the present technology.
Figure 6:
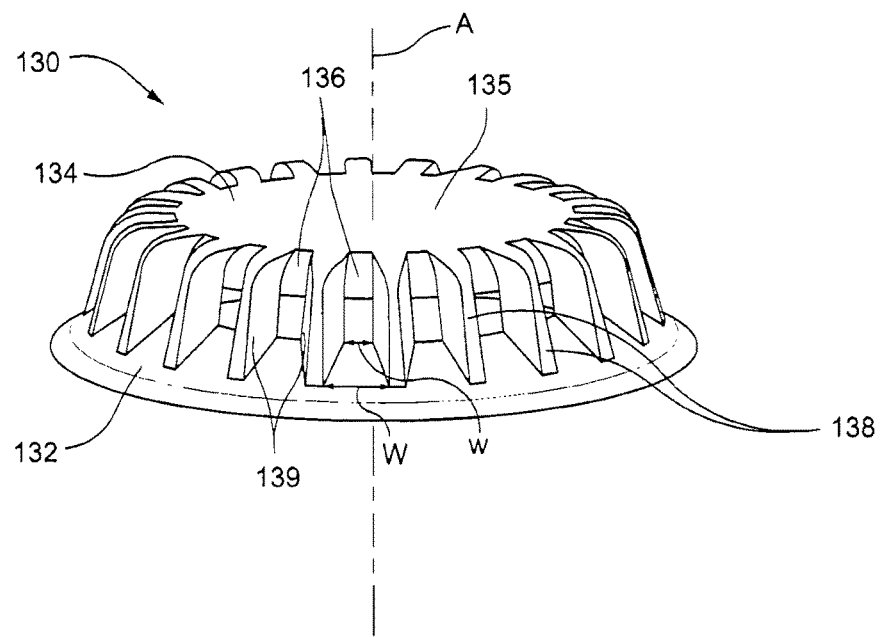
FIG. 6 is a perspective view of a gas washout vent arrangement according to another example of the present technology.

FIGS. 5 and 6 illustrate a vent cap 130 having tapered supports 138 formed between the second wall 134 and the first wall 132. The supports 138 are tapered such that a thickness of the supports decreases moving away from a center of the vent cap 138. A distance between the supports 138 thus increases moving away from the center of the vent cap 138. A distance between the supports w is at a minimum at an end of the supports closest to a center of the vent cap 130, while a distance between the supports W is at a maximum at an end of the supports farthest from the center of the vent cap 130. The side walls 139 of the supports 138 get farther apart from each other moving away from the of the vent cap 130.

Additionally, the first wall 132 is angled downward moving away from the center of the vent cap 130. Further, the second wall 134 may include a top surface 135 that is concave. These features help to enhance runoff of any water beads, and thus reduce noise.

In an alternative form, the distance between the supports w is at a maximum at an end of the supports closest to a center of the vent cap 130, while a distance between the supports W is at a minimum at an end of the supports farthest from the center of the vent cap 130. This may advantageously increase the velocity of the air at the exit point or at an end of the supports farthest from the center of the vent cap 130. This air travelling at a higher velocity may more readily drive water away from the first wall 132, thereby preventing the water from accumulating near the vent holes 136.

2.3 Increased Cavity Area

Figure 9:
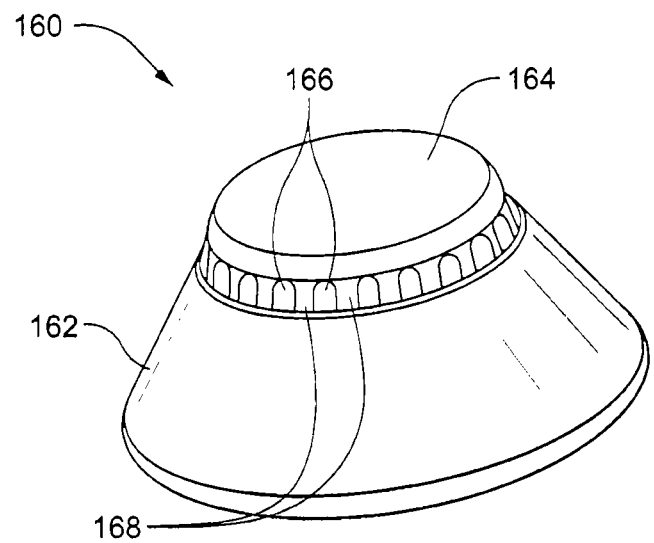
FIG. 9 is a perspective view of a gas washout vent according to another example of the present technology.

FIG. 9 illustrates a vent cap 160 according to another example of the present technology. The vent cap 160 includes a downwardly angled first wall 162, a second wall 164, supports 168 extending between the first wall 162 and the second wall 164, and a plurality of vent holes 166 between the supports 168. In this example, the vent cap 160 has an increased cavity area or increased length of travel for the air to exit through the vent holes, which is achieved by increasing a height of the first wall 162. The height of the first wall 162 may be 3 to 10 times a height of the second wall 164, for example. The increased cavity area inside the vent cap 160 may decrease the noise of the vent cap to a lower value, e.g., by 0.5 to 1.0 dBA. This may be due to the increased length of the flow path of the air thereby allowing the air to form laminar flow streams that are quieter than turbulent flow streams, for example.

2.4 Taller Thinner Vent Holes

Figure 10:
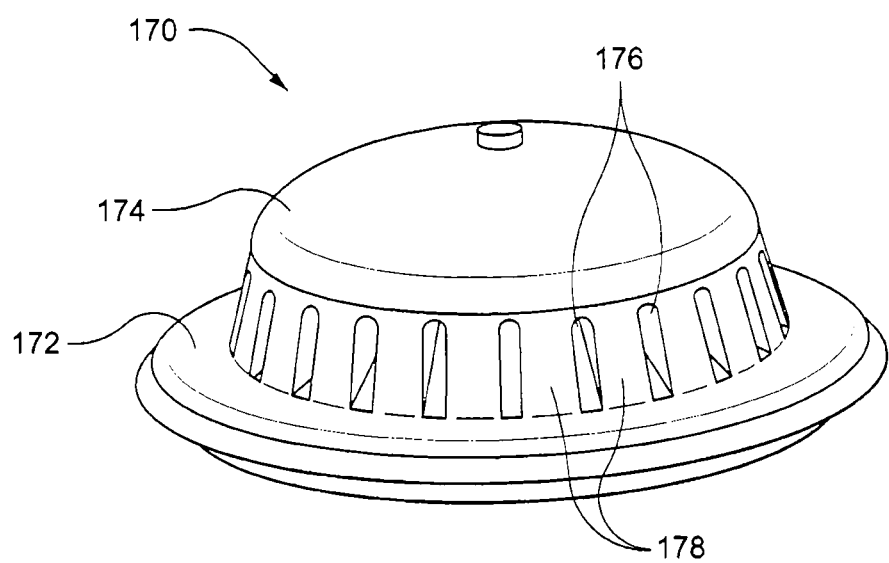
FIG. 10 is a perspective view of a gas washout vent according to another example of the present technology.

FIG. 10 illustrates a vent cap 160 according to another example of the present technology. The vent cap 160 includes a first wall 172, a second wall 174, a plurality of supports 178 extending between the first wall 172 and the second wall 174, and a plurality of vent holes 176 disposed between the supports 178. The vent holes 176 have an increased height as compared to other examples of the present technology, and may have an increased height-to-width ratio, e.g., between about 2 to 1 and 20 to 1, or between about 4 to 1 and 10 to 1. The increased height to width ratio results in the noise of the vent cap being an improved value, e.g., 1.0 to 2.0 dBA lower.

2.5 More Numerous Holes

Figure 11:
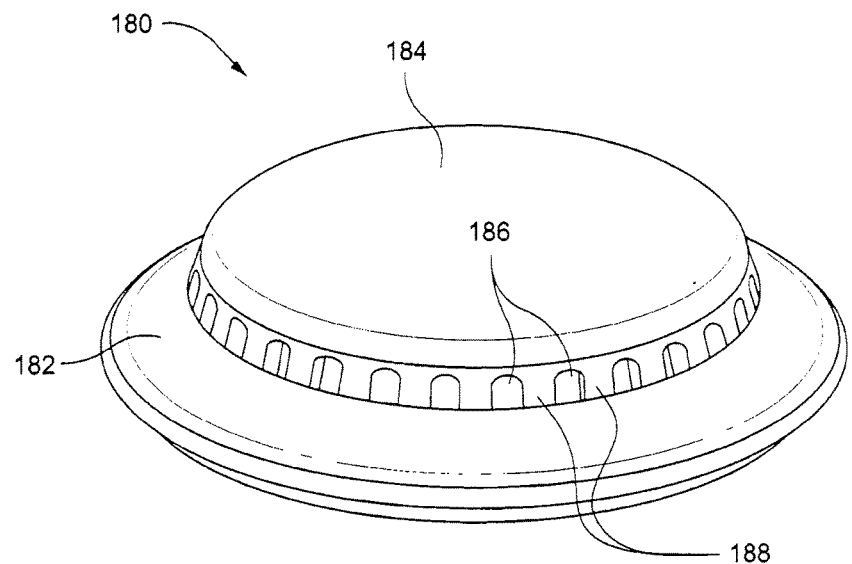
FIG. 11 is a perspective view of a gas washout vent according to another example of the present technology.
Figure 12:
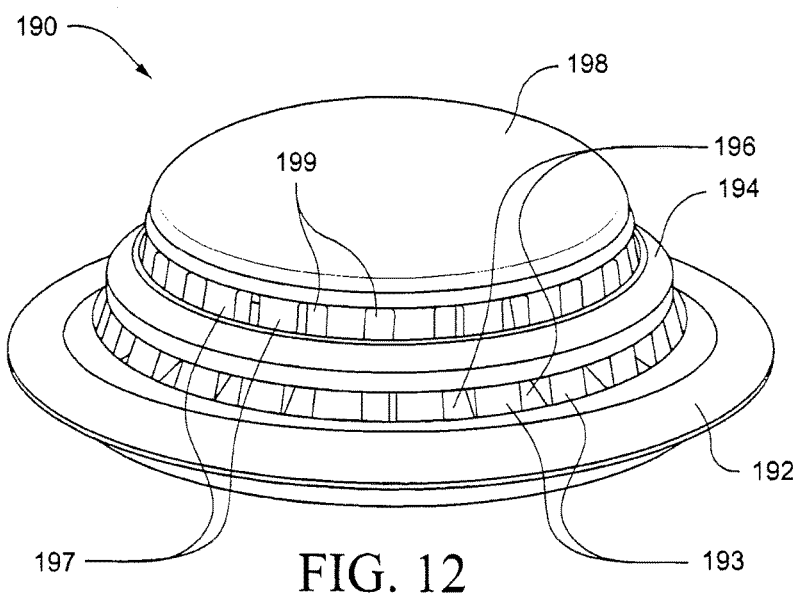
FIG. 12 is a perspective view of a gas washout vent having two layers of vent holes according to another example of the present technology.

FIGS. 11 and 12 illustrate examples of the present technology in which the number of vent holes is increased. In the vent cap 180 of FIG. 11, the first wall 182 is spaced from the second wall 184 by supports 188, with a plurality of vent holes 186 between the supports 188. The number of vent holes 186 may be thirty vent holes as compared to twenty-two vent holes which may be used in other examples, although other numbers of vent holes could also be used. The vent holes 186 are smaller than vent holes used in an example with fewer vent holes. Smaller holes may be preferable as they direct air flows in such a way that they become more fully developed, laminar flows. The number of vent holes may vary. For example, the number of vent holes may be 10-30 or more, 20-40 or more, 5, 10, 15, 20, 25, 30, 35, 40, 50, 60, 70, 80, 90, 100 or more.

FIG. 12 illustrates a "double decker" vent cap 190, which has a first wall 192, an intermediate wall 194, a second wall 198, a first row of supports 193 between the first wall 192 and the intermediate wall 194, a first row of vent holes 196 between the first supports 193, a second row of supports 197 between the intermediate wall 194 and the second wall 198, and a second row of vent holes 199 between the second supports 197. Two or more rows of vent holes further diffuses flow out of the vent holes and may aid in driving water droplets away from the vent holes, particularly those water droplets that may accumulate near intermediate wall 194 and first wall 192.

The distance of the intermediate wall 194 from a central axis of the vent cap 190 may be greater than the distance of the second wall 198 from a central axis of the vent cap 190, as illustrated in FIG. 12, or they could be a same distance. By utilizing two or more rows of vent walls, the air flow may be further diffused. In the instance where the distance of the intermediate wall 194 from a central axis of the vent cap 190 is greater than the distance of the second wall 198 from a central axis of the vent cap 190, a number of the vent holes 196 may be greater than a number of the vent holes 199. Also, the size and/or shape of the vent holes 196 may be the same as or different from the size and/or shape of the vent holes 199. Further, more than two rows of vent holes could be used. The number of vent holes may be 10-30 or more, 20-40 or more, 5, 10, 15, 20, 25, 30, 35, 40, 50, 60, 70, 80, 90, 100 or more.

FIGS. 22-29 show an example a "double decker" type vent cap 390 provided to an elbow 306 according to an example of the present technology. In the illustrated example, the vent cap is integrally formed in one-piece with the elbow. This arrangement provides a single piece elbow with no removable parts, e.g., so patients do not have to disassemble the elbow for cleaning. In an alternative example, the vent cap may be formed separately from the elbow and attached thereto, e.g., releasably attached. Also, it should be appreciated that the vent cap may be provided (e.g., integrally formed, attached) to other portions of the mask, e.g., mask frame.

As illustrated, the elbow 306 includes a first end 310 for releasably engaging with an opening in a mask frame and a second end 312 for releasably engaging with an air delivery tube, e.g., via a swivel provided to the second end. In the illustrated example, the first end 310 includes opposing ribs 311 adapted to engage the mask frame with a snap-fit. The second end 312 includes a plurality of resilient flexible arms 307, e.g., adapted to engage the swivel with a snap-fit. However, the first and second ends may include other suitable structures for engaging the frame/swivel.

Figure 26:
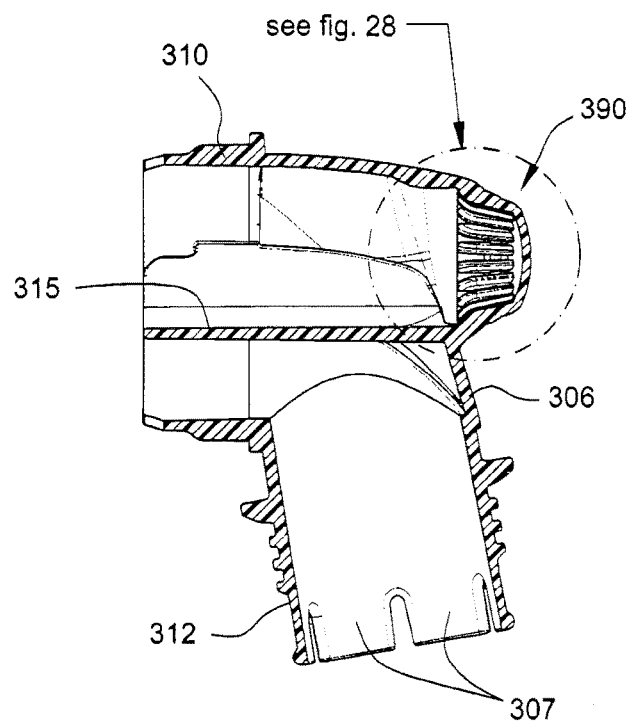
FIG. 26 is a cross-sectional view through line 26-26 of FIG. 23.
Figure 27:
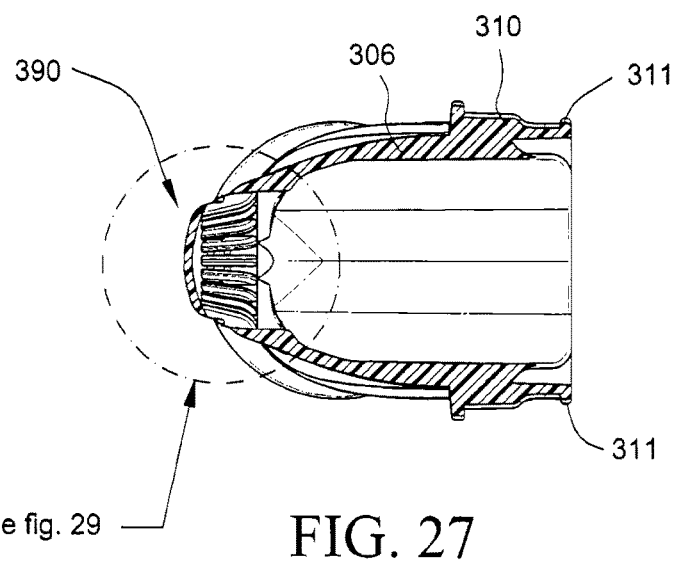
FIG. 27 is a cross-sectional view through line 27-27 of FIG. 23.

As best shown in FIG. 26, the elbow 306 includes a baffle 315 adjacent to where the elbow is attached to the mask frame. The baffle is arranged to divide the upper arm of the elbow into an air delivery passage and an exhaust passage, e.g., to enhance $CO_2$ washout.

Figure 25:
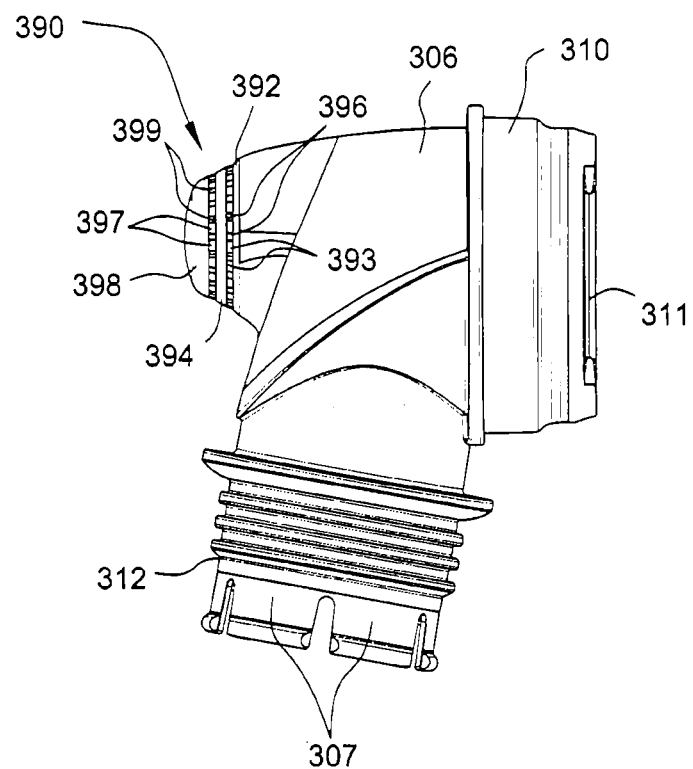
FIG. 25 is a side view of the elbow of FIG. 22.
Figure 28:
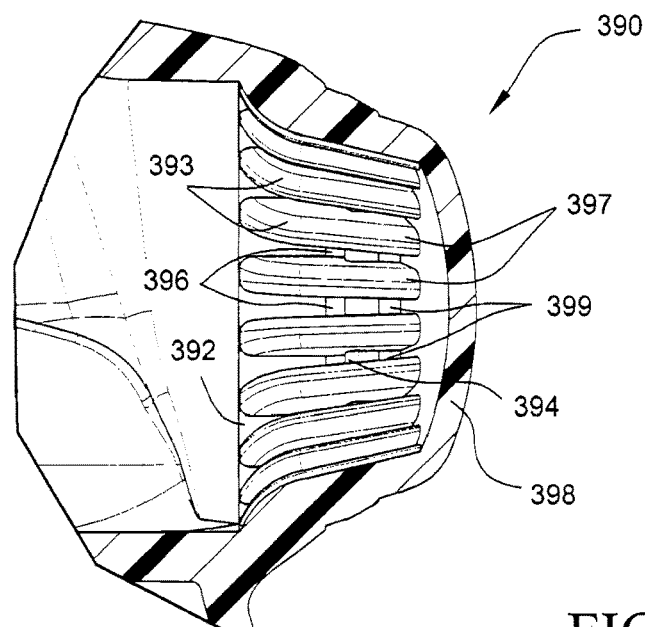
FIG. 28 is an enlarged view of a portion of FIG. 26.
Figure 29:
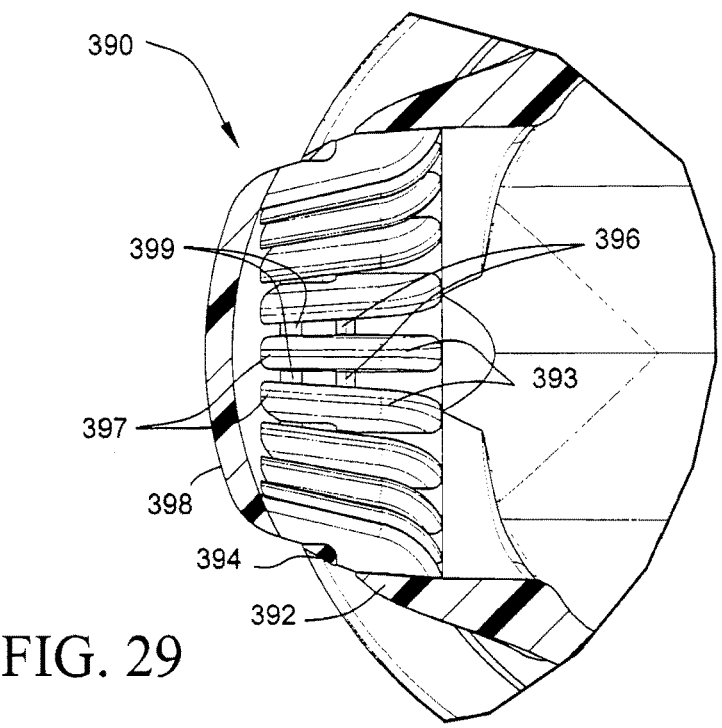
FIG. 29 is an enlarged view of a portion of FIG. 27.
Figure 34:
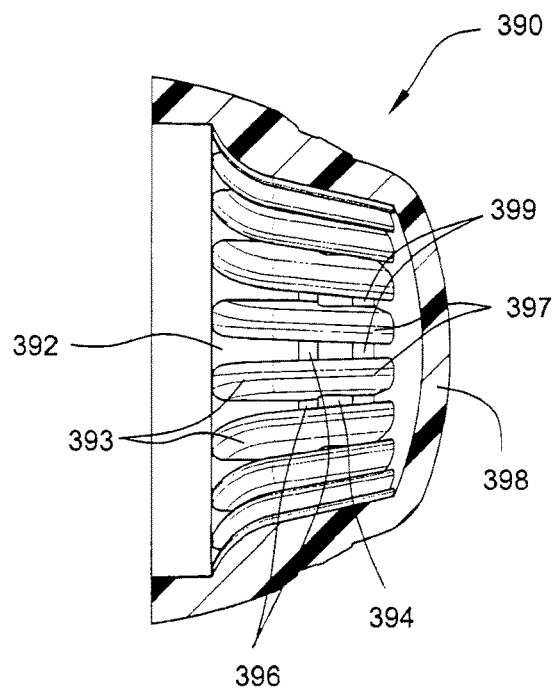
FIG. 34 is a cross-sectional view through line 34-34 of FIG. 33.
Figure 35:
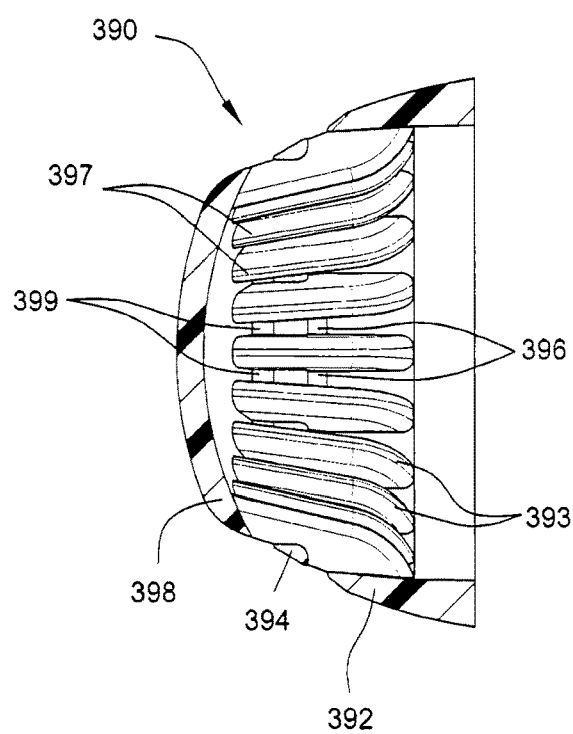
FIG. 35 is a cross-sectional view through line 35-35 of FIG. 33.

The main body of the elbow 306 includes the vent cap 390 integrally formed in one-piece therewith. Similar to the vent cap 190 of FIG. 12 described above, the vent cap includes a first wall 392, an intermediate wall 394, a second wall 398, a first row of supports 393 between the first wall 392 and the intermediate wall 394, a first row of vent holes 396 between the first supports 393, a second row of supports 397 between the intermediate wall 394 and the second wall 398, and a second row of vent holes 399 between the second supports 397, as best shown in FIGS. 25, 28, and 29. As shown in FIGS. 28 and 29, the first and second row of supports 393, 397 may be provided by a single row of supports that extends from the first wall 392, across the intermediate wall 394, to the second wall 398 to define the first and second row of vent holes 396, 399.

FIGS. 30-35 show the vent cap 390 isolated from the elbow. In this arrangement, the vent cap 390 may be removably attachable to an elbow by, for example, a bayonet connection, tongue and groove, clip or other attachment mechanism.

In alternative examples, there may be more than two rows of vents, for example there may be 3, 4, 5, 6 or more rows of vents.

By adding an additional row of vent holes, the vent holes may be made smaller while maintaining the vent flow (compared to a vent having only a single row of vent holes). Since the vent holes may be smaller in diameter, the velocity of the air exiting the vent holes may be higher than the velocity of air exiting a vent with only a single row of vent holes with a larger diameter. This increased velocity of air exiting the vent holes may aid in driving water droplets away from the surfaces surrounding the vent holes.

2.6 Baffle

Figure 13:
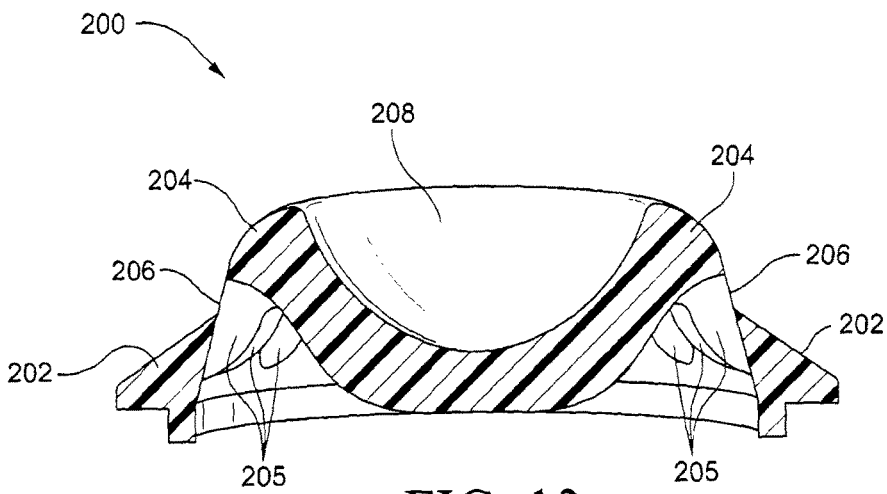
FIG. 13 is a cross-sectional view of a gas washout vent according to another example of the present technology.
Figure 14:
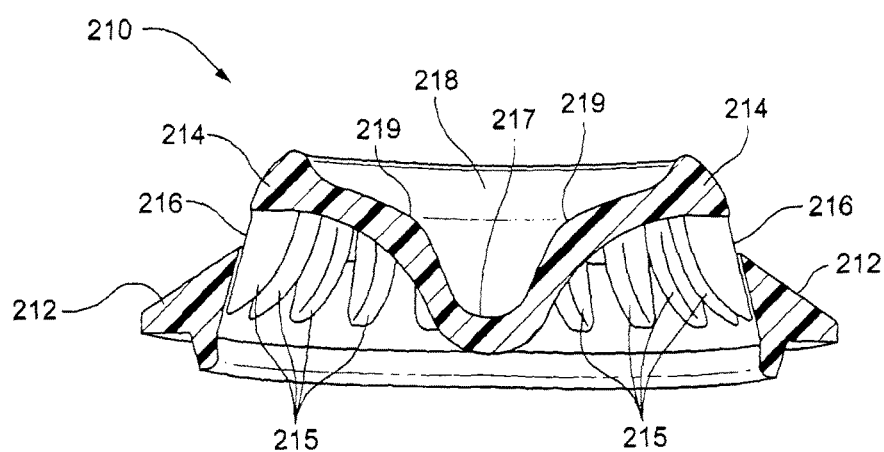
FIG. 14 is a cross-sectional view of a gas washout vent according to another example of the present technology.
Figure 15:
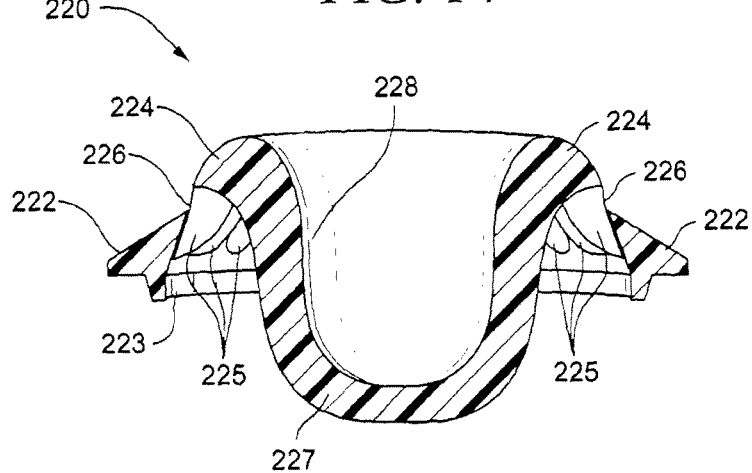
FIG. 15 is a cross-sectional view of a gas washout vent according to another example of the present technology.

FIGS. 13-15 illustrate cross-sectional views of examples of the present technology that include a baffle to direct the flow of gas inside the vent cap to the vent holes. The vent cap 200 illustrated in FIG. 13 includes a first wall 202, a baffle 208 having an outer edge forming a second wall 204, a plurality of supports 205 formed between the first wall 202 and the second wall 204, and a plurality of vent holes 206 formed between the supports 205. The baffle 208 may have a concave shape. Additionally, the vent cap 200 may include twenty-two or thirty vent holes 206. The number of vent holes 206 may be 10-30 or more, 20-40 or more, 5, 10, 15, 20, 25, 30, 35, 40, 50, 60, 70, 80, 90, 100 or more.

The vent cap 210 illustrated in FIG. 14 includes a first wall 212, a baffle 218 having an outer edge forming a second wall 214, a plurality of supports 215 formed between the first wall 212 and the second wall 214, and a plurality of vent holes 216 formed between the supports 215. The baffle 218 includes a central portion 217 having a generally concave shape, and a convex portion 219. The vent cap 210 may include twenty-two or thirty vent holes 216. The baffle 218 may have undulations or curves formed by the central portion 217 having a generally concave shape, and a convex portion 219, to force the air to flow over a larger area before exiting the vent cap 210. This will slow the flow of the air producing low velocity, fully developed, laminar flow, which may be quieter. This may also encourage water droplets to form on the baffle, and once formed on the baffle, drain back into the mask.

The vent cap 220 illustrated in FIG. 15 includes a first wall 222, a baffle 228 having an outer edge forming a second wall 224, a plurality of supports 225 formed between the first wall 222 and the second wall 224, and a plurality of vent holes 226 formed between the supports 225. The baffle 228 has a generally concave shape. The vent cap 220 may include twenty-two or thirty vent holes 206. The first wall 222 may have a first edge 223, and the baffle may have a central portion 227 that extends below the first edge 223 (e.g., into the shell or breathing cavity). This will result in the central portion 227 of the baffle 228 extending into an interior of the mask when the vent cap 220 is on the mask. This arrangement may better separate exhausted gases with incoming gases because the baffle extends into the mask.

The arrangement of FIG. 13 may direct air flow from inside the mask to outside the vents in a path substantially similar to the curvature of the baffle. This direction of air flow may be generally away from the patient but towards the bed partner. The arrangement of FIG. 14 may direct air flow from inside the mask to outside the vents in a path substantially similar to the convex portion 219. This may be more desirable as the air flow may be directed away from the bed partner.

2.7 Channels To Guide Gas Flow

Figure 17:
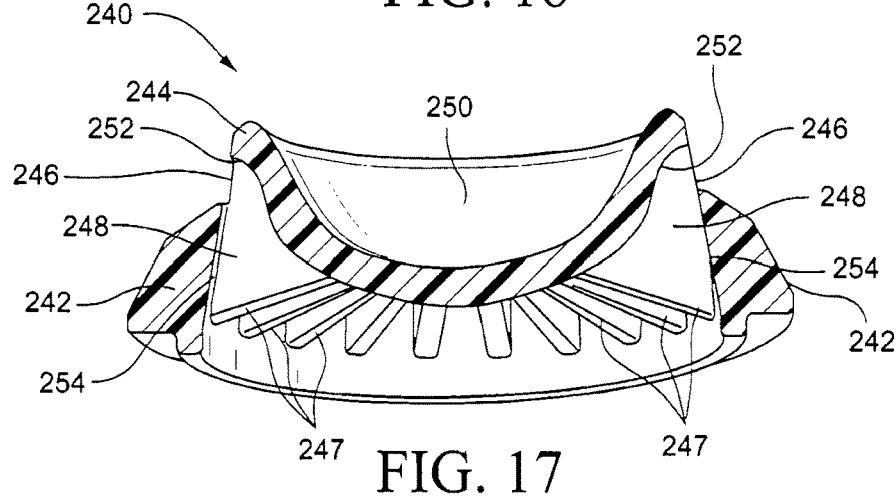
FIG. 17 is a cross-sectional view of a gas washout vent according to another example of the present technology.
Figure 18:
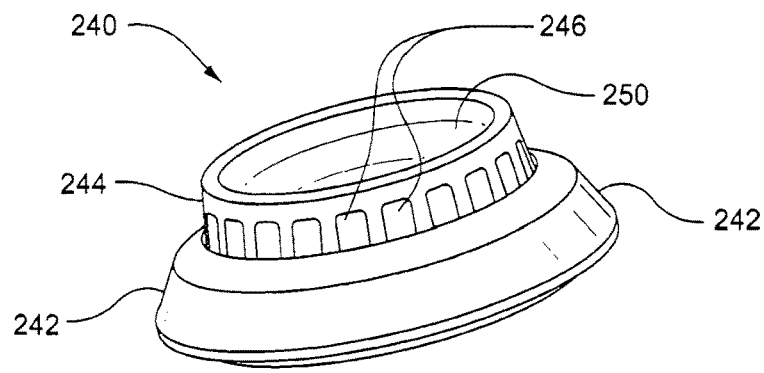
FIG. 18 is a perspective view of a gas washout vent according to another example of the present technology.
Figure 19:
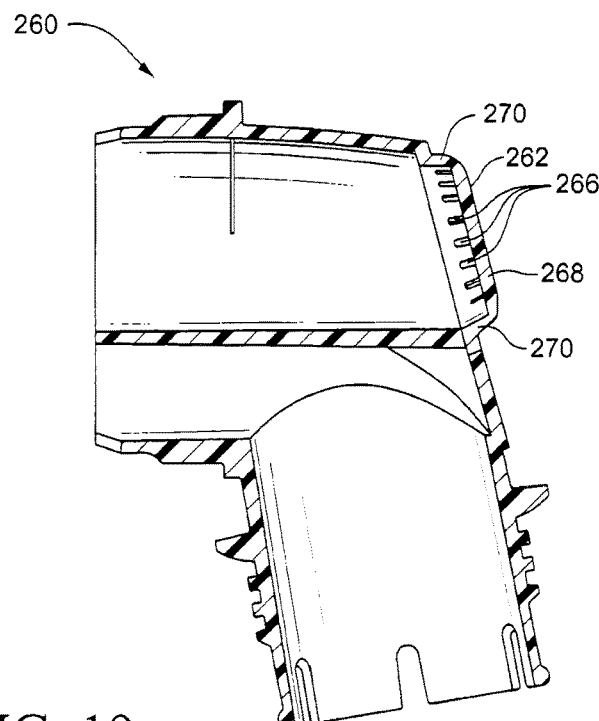
FIG. 19 is a cross-sectional view of a prior art elbow having a gas washout vent.
Figure 20:
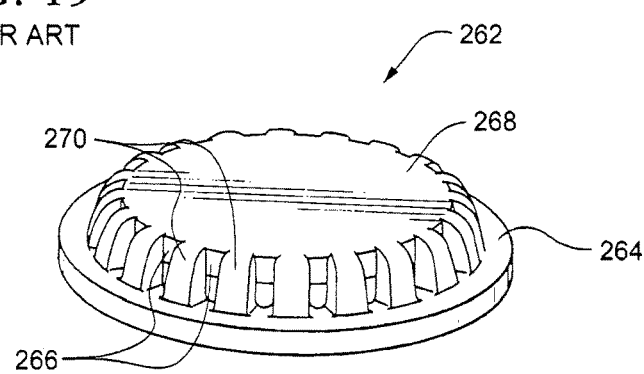
FIG. 20 is a perspective view of a prior art gas washout vent.
Figure 21:
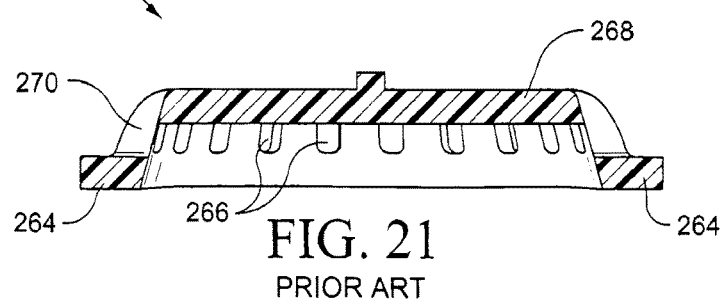
FIG. 21 is a cross-sectional view of the gas washout vent of FIG. 20.
Figure 22:
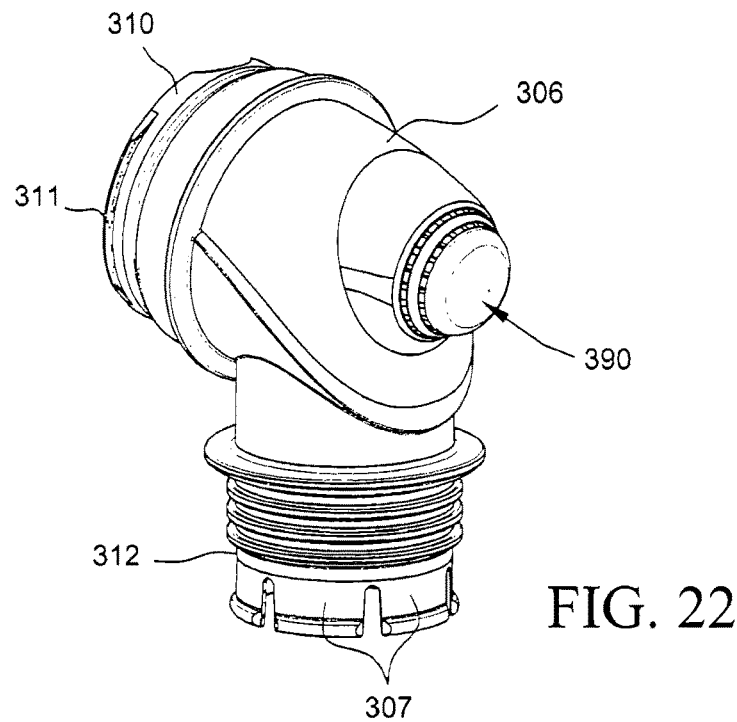
FIG. 22 is a perspective view of an elbow including a gas washout vent according to an example of the present technology.
Figure 23:
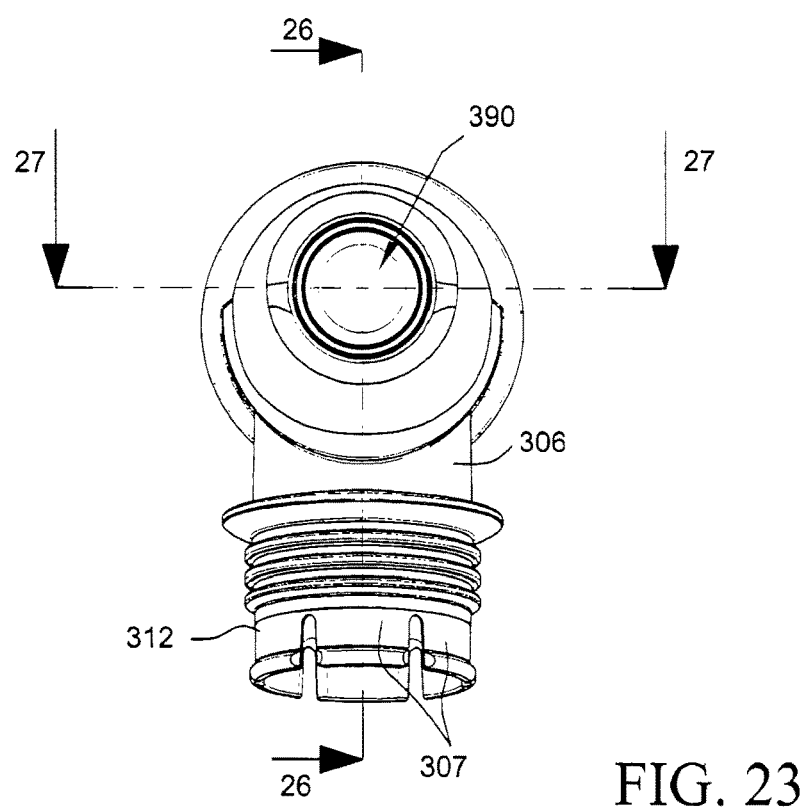
FIG. 23 is a front view of the elbow of FIG. 22.
Figure 24:
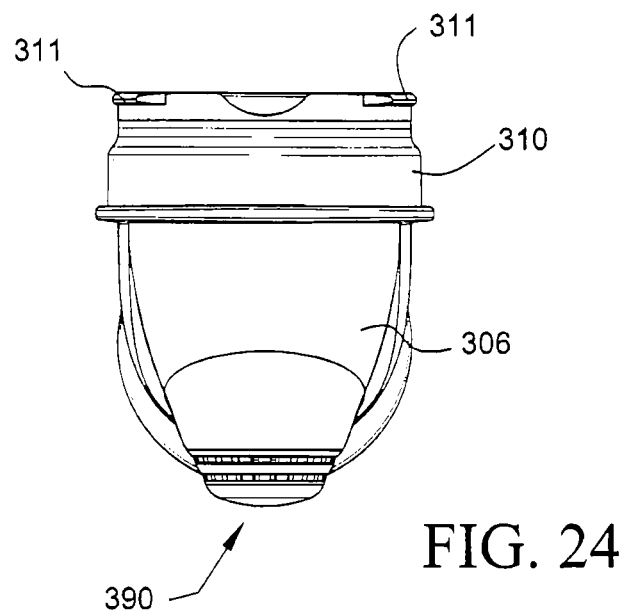
FIG. 24 is a top view of the elbow of FIG. 22.

Examples of the present technology may use the supports between the second wall and the first wall to form channels to guide the air to each vent hole. As illustrated in FIGS. 17 and 18, the vent cap 240 includes a first wall 242, a second wall 244, supports 247 extending between the first wall 242 and the second wall 244, and a plurality of vent holes 246 formed between the supports 247. The first wall 242 may be disposed radially outward of the outer edge of baffle 250, which may have a concave shape. Channels 248 may extend between the supports 247, an inner edge 254 of the first wall 242, and a bottom surface 252 of the baffle 250.

The channels 248 may vary in a thickness measured between the inner edge 254 of the first wall 242 and the bottom surface 252 of the baffle 250. The thickness of the channels 248 may decrease as air flows from inside the vent cap 240 to the vent holes 246. The bottom surface 252 of the baffle 250 may be curved inside the channels 248 to force the air to flow over a larger area before exiting the vent cap 210. Further, the supports 247 include a first edge that extends within the vent cap 220 in a direction substantially perpendicular to a central axis of the vent cap 220.

The concave shape of the baffle 250 causes the supports 247 to taper in a direction defined by the vent holes to the central axis of the vent cap 240. This tapering may cause the air flow to increase velocity towards the exit of the vent hole and hence be quieter and assist in driving water droplets from areas surrounding the vent holes. The length of the supports (i.e., from the top of baffle 250 to inner edge 254) further allows the air to develop to laminar flow, thereby reducing the noise of the air exiting the vent.

2.8 Inwardly Facing Vent

Figure 16:
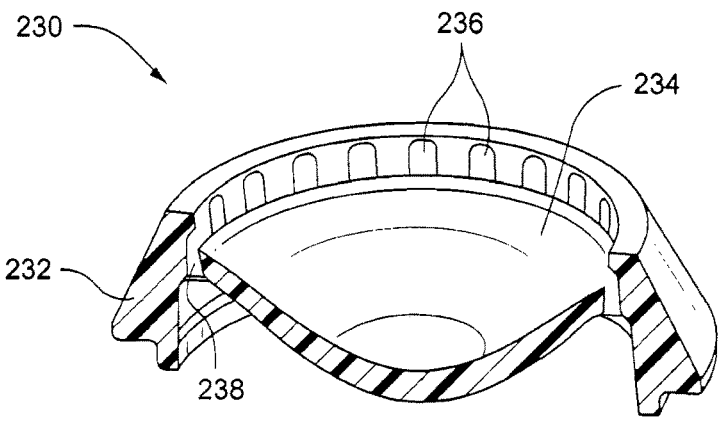
FIG. 16 is a cross-sectional view of a gas washout vent according to another example of the present technology.

As illustrated in FIG. 16, vent cap 230 includes an outer wall 232, a baffle 234, and a plurality of inwardly facing vent holes 236 disposed in an inner surface of the outer wall 232. The vent holes 236 communicate with the interior of the vent cap 230 via channels 238 formed between the inside surface of the outer wall 232 and the outer edge of the baffle 234.

The vent holes 236 may be disposed around the entire inner surface of the outer wall 232, and may be evenly spaced. The vent holes 236 may be adapted to be selectively blockable, such that some of the vent holes 236 may be blocked while others remain open. For example, the vent cap 230 may be adapted to include plugs or other structure for selectively blocking some of the vent holes 236 while other vent holes remain open. In particular, it may be beneficial to block any upwardly pointing vent holes to keep the venting air away from the user's eyes.

2.9 Vent Hole Variations

Figure 7:
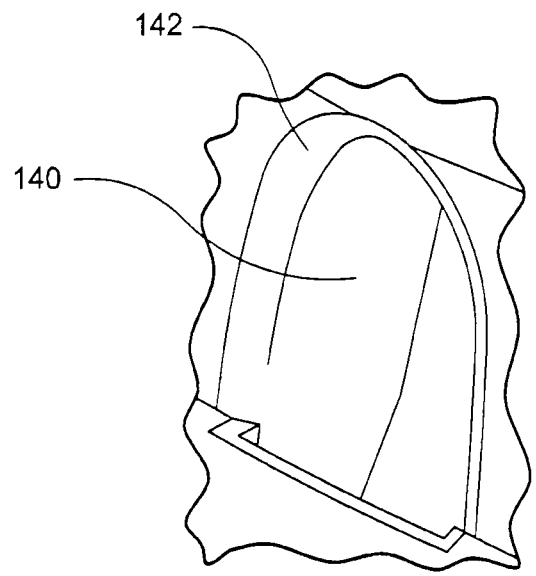
FIG. 7 is a partial perspective view of a vent hole of a gas washout vent according to another example of the present technology.

The vent holes may be formed in various shapes and/or sizes. For example, as illustrated in FIG. 7, the vent hole 140 may include a rounded edge 142. The vent holes 140 may include rounded second corners adjacent the second wall and squared off first corners adjacent the first wall as illustrated in FIGS. 3, 7 and 9-11, or may alternatively include rounded off first corners adjacent the first wall and squared off second corners adjacent the second wall as illustrated in FIG. 5. Alternatively, the vent holes may have all corners rounded off to be in a circular, elliptical or other rounded shape.

The vent holes may be evenly spaced around the vent insert, and may be positioned in a substantially circular configuration. In an alternative example, the vent holes may be in evenly spaced about the vent insert. In a further example, the vent holes may be positioned in a non-circular configuration, e.g., elliptical, square.

Figure 8:
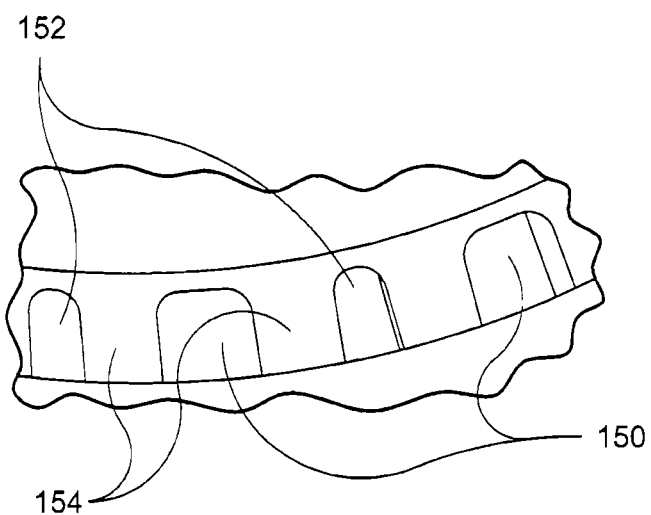
FIG. 8 is a partial perspective view of a gas washout vent having vent having vent holes of differing sizes according to another example of the present technology.

The vent holes may also include shorter, wider vent holes, such as vent holes 150 illustrated in FIG. 8. These vent holes may have an approximately equal width and height, and may include any of the rounded corners described above. Where the vent holes are shorter and wider such as vent holes 150, the supports 154 between the vent holes may also be shorter and/or wider. Additionally, the vent holes may include smaller vent holes alternately disposed with bigger vent holes, such as the smaller vent holes 152 alternately disposed with the larger vent holes 150. Further, the vent holes may be adapted to alternately block and unblock every second vent hole so that flow of the air may be swapped between two groups of vent holes.

The amount of generated vent noise is very sensitive to the difference in velocity between the exit vent flow and the velocity of the air surrounding the exit vent stream (i.e., typically the ambient air, which is relatively still).

By having variation in the size and length of adjacent vent orifices, differences in adjacent exit vent velocities are created since jet stream velocity is dependent on orifice size and flow path length. This can effectively reduce the velocity gradient between the exhaust streams and the still ambient air.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. Furthermore, each individual component of any given assembly, one or more portions of an individual component of any given assembly, and various combinations of components from one or more examples may include one or more ornamental design features. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A vent for a mask used for positive airway pressure treatment of sleep disordered breathing, the vent being constructed and arranged to discharge exhaled gas from an interior of the mask to atmosphere, the vent comprising:
   a first wall having an inner side face and a top face;
   a second wall having a top surface and a bottom surface;
   a plurality of spaced supports disposed between the first wall and the second wall, each of the supports having a top face in contact with the bottom surface of the second wall and an outer side face in contact with the inner side face of the first wall; and
   at least one vent hole disposed between adjacent supports, wherein the first wall provides a lower edge of the at least one vent hole and the second wall provides an upper edge of the at least one vent hole, and
   wherein each of the supports comprises an inner side face, the inner side face including a generally convex shape to guide exhaled gas to the at least one vent hole.

2. The vent according to claim 1, wherein the inner side face of the first wall is inwardly angled.

3. The vent according to claim 1, wherein the second wall has a convex shape.

4. The vent according to claim 1, wherein the second wall has a concave shape.

5. The vent according to claim 1, wherein the second wall has a concave portion and a convex portion.

6. The vent according to claim 1, wherein the top face of the first wall is downwardly angled moving away from a central axis of the vent.

7. The vent according to claim 1, wherein the top face of the first wall has a convex shape.

8. The vent according to claim 1, wherein the at least one vent hole includes a plurality of vent holes that are evenly spaced around the vent.

9. The vent according to claim 1, wherein the at least one vent hole includes a plurality of vent holes that are spaced in a circular configuration around the vent.

10. The vent according to claim 1, wherein the at least one vent hole includes a plurality of vent holes and all of the vent holes have a common shape.

11. The vent according to claim 1, wherein the at least one vent hole includes a plurality of vent holes and alternating ones of the vent holes have a different size.

12. The vent according to claim 1, wherein the at least one vent hole includes a plurality of vent holes and the vent holes include at least one rounded corner.

13. The vent according to claim 1, wherein the second wall comprises a baffle adapted to direct a flow of air inside the vent.

14. The vent according to claim 1, wherein the bottom surface of the second wall, the inner side face of the first wall and the supports combine to direct a flow of air inside the vent to the vent holes.

15. The vent according to claim 1, wherein the inner side face of the first wall and the bottom surface of the second wall define an air flow channel to guide air flow to the at least one vent hole, and the air flow channel includes a thickness measured between the inner side face of the first wall and the bottom surface of the second wall that gradually decreases as air flows towards the vent hole.

16. The vent according to claim 1, wherein the first wall includes a first edge, and the second wall includes a central portion that extends below the first edge of the first wall.

17. The vent according to claim 1, wherein the supports include a first edge that extends within the vent in a direction substantially perpendicular to a central axis of the vent.

18. The vent according to claim 1, wherein the generally convex shape extends along a width of the inner side face of each of the supports.

19. The vent according to claim 1, wherein the generally convex shape extends along a length of the inner side face of each of the supports.

20. The vent according to claim 1, wherein adjacent supports, the inner side face of the first wall, and the bottom surface of the second wall form a channel leading to the at least one vent hole.

21. The vent according to claim 20, wherein at least a portion of the channel comprises a curved shape to guide exhaled gas to the at least one vent hole.

22. The vent according to claim 1, wherein the second wall includes an outer edge forming an outer perimeter, the outer edge comprising a continuous, generally circular, closed shape.

23. The vent according to claim 1, wherein the inner side face of the first wall is positioned outside an outer perimeter of the supports and outside an outer perimeter of the second wall.

24. A mask comprising:
a frame;
an interface provided to the frame; and
the vent according to claim 1.

25. The mask according to claim 24, wherein the interface comprises a cushion, prongs or nozzles.

26. The mask according to claim 24, wherein at least a portion of the vent and the frame comprises a one-piece construction.

27. The mask according to claim 24, wherein the vent is selectably detachable from and attachable to the frame.

28. The mask according to claim 24, further comprising an elbow provided to the frame, and the vent is selectably detachable from and attachable to the elbow.

29. A vent for a mask used for positive airway pressure treatment of sleep disordered breathing, the vent being constructed and arranged to discharge exhaled gas from an interior of the mask to atmosphere, the vent comprising:
a first wall; and
a second wall having an outer edge forming an outer perimeter;
a support structure located between the first wall and the second wall; and
at least one gas washout vent hole located between the first wall and the outer edge of the second wall,
wherein the at least one gas washout vent hole includes an inner edge positioned inside the outer perimeter of the second wall, and
wherein the first wall includes an inner edge positioned outside the support structure, and the inner edge of the first wall provides a lower edge of the at least one gas washout vent hole.

30. The vent according to claim 29, wherein the support structure includes a plurality of spaced support walls positioned between the first wall and the second wall.

31. The vent according to claim 30, wherein the at least one gas washout vent hole is disposed between adjacent support walls.

32. The vent according to claim 30, wherein each of the support walls includes a first edge that extends within the vent in a direction substantially perpendicular to a central axis of the vent.

33. The vent according to claim 30, wherein the first wall comprises an inner side face and a top face, and the second wall comprises a top surface and a bottom surface.

34. The vent according to claim 33, wherein each of the support walls comprises an upper face disposed adjacent to the bottom surface of the second wall, and a side face disposed adjacent to the inner side face of the first wall.

35. The vent according to claim 33, wherein the inner side face of the first wall is an inwardly angled side surface positioned adjacent to a side face of each of the support walls.

36. The vent according to claim 33, wherein the bottom surface of the second wall, the inner side face of the first wall and the support walls combine to direct a flow of air inside the vent to the at least one gas washout vent hole.

37. The vent according to claim 33, wherein the second wall comprises a baffle and an air flow chamber formed between the inner side face of the first wall and the baffle gradually decreases in width as air flows towards the at least one gas washout vent hole.

38. The vent according to claim 30, wherein each of the support walls gradually decreases in width moving away from a central axis of the vent.

39. The vent according to claim 30, wherein a distance between adjacent ones of the support walls gradually increases moving away from a central axis of the vent.

40. The vent according to claim 29, wherein the second wall comprises a baffle adapted to direct a flow of air inside the vent.

41. The vent according to claim 29, wherein the second wall has a convex shape.

42. The vent according to claim 29, wherein the second wall has a concave shape.

43. The vent according to claim 29, wherein the second wall has a concave portion and a convex portion.

44. The vent according to claim 29, wherein the first wall includes a top face that is downwardly angled moving away from a central axis of the vent.

45. The vent according to claim 44, wherein the top face of the first wall has a convex shape.

46. The vent according to claim 29, wherein the at least one gas washout vent hole includes a plurality of vent holes that are evenly spaced around the vent.

47. The vent according to claim 29, wherein the at least one gas washout vent hole includes a plurality of vent holes that are spaced in a circular configuration around the vent.

48. The vent according to claim 29, wherein the at least one gas washout vent hole includes a plurality of vent holes and all of the vent holes have a common shape.

49. The vent according to claim 29, wherein the at least one gas washout vent hole includes a plurality of vent holes and the vent holes include at least one rounded corner.

50. The vent according to claim 29, wherein the at least one gas washout vent hole includes a plurality of vent holes, and the vent holes are arranged in a first row of vent holes and a second row of vent holes displaced from the first row of vent holes.

51. The vent according to claim 29, wherein the inner edge of the first wall is positioned outside an outer perimeter of the support structure.

52. A mask for use in positive airway pressure treatment of sleep disordered breathing, the mask having an interior and an exterior, the mask being configured to receive a supply of air or other breathable gas pressurized above atmospheric pressure to the interior, the mask comprising:
   a shell or frame;
   a patient contacting portion to form a seal with a patient's face; and
   the vent according to claim 29 to discharge gas exhaled by the patient from the interior to the exterior.

* * * * *